United States Patent
Hanes et al.

(10) Patent No.: US 10,668,025 B2
(45) Date of Patent: *Jun. 2, 2020

(54) MUCUS PENETRATING PARTICLES WITH HIGH MOLECULAR WEIGHT AND DENSE COATINGS

(71) Applicant: The Johns Hopkins University, Baltimore, MD (US)

(72) Inventors: Justin Hanes, Baltimore, MD (US); Katharina Maisel, Troy, MI (US); Laura Ensign, Towson, MD (US); Richard Cone, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/771,961

(22) PCT Filed: Oct. 31, 2016

(86) PCT No.: PCT/US2016/059661
§ 371 (c)(1),
(2) Date: Apr. 27, 2018

(87) PCT Pub. No.: WO2017/075565
PCT Pub. Date: May 4, 2017

(65) Prior Publication Data
US 2018/0221293 A1    Aug. 9, 2018

Related U.S. Application Data

(60) Provisional application No. 62/248,432, filed on Oct. 30, 2015.

(51) Int. Cl.
*A61K 9/51* (2006.01)
*A61K 9/00* (2006.01)

(52) U.S. Cl.
CPC .......... *A61K 9/5146* (2013.01); *A61K 9/0014* (2013.01); *A61K 9/0031* (2013.01);
(Continued)

(58) Field of Classification Search
None
See application file for complete search history.

(56) References Cited

U.S. PATENT DOCUMENTS 9,415,020 B2 * 8/2016 Ensign ................ A61K 9/0034
9,629,813 B2 * 4/2017 Ensign ................ A61K 9/0034
(Continued)

FOREIGN PATENT DOCUMENTS

WO    WO 95/03357    8/2005
WO    WO 2005/072710    8/2005
(Continued)

OTHER PUBLICATIONS

SK Lai, Y-Y Wang, J Hanes. "Mucus-penetrating nanoparticles for drug and gene delivery to mucosal tissues." Advanced Drug Delivery Reviews, vol. 61, 2009, pp. 158-171. (Year: 2009).*
(Continued)

*Primary Examiner* — Isaac Shomer
(74) *Attorney, Agent, or Firm* — Pabst Patent Group LLP

(57) ABSTRACT

Mucus penetrating particles (MPPs) include one or more core polymers, one or more therapeutic, prophylactic and/or diagnostic agents; and one or more surface modifying agents. The surface modifying agents coat the surface of the particle in a sufficient density to enhance the diffusion of the modified nanoparticles throughout the mucosa, relative to equivalent nanoparticles that are not surface modified. Nanoparticles can be sufficiently densely coated with poly (ethylene glycol) (PEG) with a molecular weight of from 10 kD to 40 kD or greater coated with a surface density from about 0.1 to about 100 molecules/100 nm$^2$, preferably from (Continued)

about 0.5 to about 50 molecules/100 nm$^2$, more preferably from about 0.9 to about 45 molecules/100 nm$^2$.

16 Claims, 6 Drawing Sheets

(52) U.S. Cl.
CPC .......... *A61K 9/0034* (2013.01); *A61K 9/5153* (2013.01); *Y10S 977/773* (2013.01); *Y10S 977/906* (2013.01)

(56) References Cited

U.S. PATENT DOCUMENTS

| | | | |
|---|---|---|---|
| 9,889,208 B2* | 2/2018 | Hanes | A61K 47/6911 |
| 2010/0215580 A1* | 8/2010 | Hanes | A61K 9/0034 424/9.1 |
| 2013/0183244 A1 | 7/2013 | Hanes et al. | |
| 2013/0236556 A1 | 9/2013 | Lai et al. | |

FOREIGN PATENT DOCUMENTS

| | | | | |
|---|---|---|---|---|
| WO | WO 2013/166408 | 11/2007 | | |
| WO | WO 2013/090804 | 6/2013 | | |
| WO | WO-2013090804 A2 * | 6/2013 | | A61K 31/12 |
| WO | WO 2013/110028 | 7/2013 | | |
| WO | WO-2013110028 A1 * | 7/2013 | | A61K 9/0034 |

OTHER PUBLICATIONS

EA Nance, GF Woodworth, KA Sailor, T-Y Shih, Q Xu, G Swaminathan, D Xiang, C Eberhart, J Hanes. "A Dense Poly(Ethylene Glycol) Coating Improves Penetration of Large Polymeric Nanoparticles Within Brain Tissue." Science Translational Medicine, vol. 4 Issue 149, 2012, pp. 1-8. (Year: 2012).*
LM Ensign, C Schneider, JS Suk, R Cone, J Hanes. "Mucus Penetrating Nanoparticles: Biophysical Tool and Method of Drug and Gene Delivery." Advanced Materials, vol. 24, 2012, pp. 3887-3894. (Year: 2012).*
Asscher, et al., "Cornification of the human vaginal epithelium", J. Anat., 90(Pt 4):547-552 (1956).
Boskey, et al., "A self-sampling method to obtain large volumes of undiluted cervicovaginal secretions", Sex Transm. Dis., 30(2):107-109 (2003).
Boylan, et al., "Highly compacted DNA nanoparticles with low MW PEG coatings: in vitro, ex vivo and in vivo evaluation", J. Control. Release, 157(1):72-79 (2012).
Caliceti, et al., "Pharmacokinetic and biodistribution properties of poly(ethylene glycol)-protein conjugates", Adv. Drug Deliv. Rev., 55(10):1261-1277 (2003).
Champlin, et al., "Determining the stage of the estrous cycle in the mouse by the appearance of the vagina", Biol. Reprod., 8(4):491-494 (1973).
Cone, "Mucus", Mucosal Immunology, 3rd Edition, 49-72 (2005).
Cone, et al., "Barrier properties of mucus", Adv. Drug Deliv. Rev., 61(2):75-85 (2009).
Cu, et al., "In vivo distribution of surface-modified PLGA nanoparticles following intravaginal delivery", J. Control. Release, 156(2):258-264 (2011).
Cu, et al., "Controlled surface modification with poly(ethylene)glycol enhances diffusion of PLGA nanoparticles in human cervical mucus", Mol. Pharm., 6(1):173-181 (2009).
Da Silva, et al., "DNA nanoparticle-mediated thymulin gene therapy prevents airway remodeling in experimental allergic asthma", J. Control. Release, 180:125-133 (2014).
Das Neves, et al., "Gels as vaginal drug delivery systems", Int. J. Pharm., 318(1-2):1-14 (2006).
Dawson, et al., "Transport of polymeric nanoparticle gene carriers in gastric mucus", Biotechnol. Prog., 20(3):851-857 (2004).

Deascentiis, et al., "Mucoadhesion of poly(2-hydroxyethyl methacrylate) is improved when linear ply(ethylene oxide) chains are added to the polymer network", J. Control. Release, 33(1):197-201 (1995).
Dreborg, et al., "Immunotherapy with monomethoxypolyethylene glycol modified allergens", Crit. Rev. Ther. Drug Carrier Syst., 6(4):315-365 (1990).
Du, et al., "Grafted poly-(ethylene glycol) on lipid surfaces inhibits protein adsorption and cell adhesion", Biochim. Biophys. Acta., 1326(2):236-248 (1997).
Ensign, et al., "Mucus-penetrating nanoparticles for vaginal drug delivery protect against herpes simplex virus", Sci. Transl. Med., 4(138):138ra79 (2012).
Ensign, et al., "Enhanced vaginal drug delivery through the use of hypotonic formulations that induce fluid uptake", Biomaterials, 34(28):6922-6929 (2013).
Ensign, et al., "Ex vivo characterization of particle tranport in mucus secretions coating freshly excised mucosal tissues", Mol. Pharm., 10(6):2176-2182 (2013).
Eyles, et al., "The transfer of polystyrene microspheres from the gastrointestinal tract to the circulation after oral administration in the rat", J. Pharm. Pharmacol., 47(7):561-565 (1995).
Huang, et al., "Molecular aspects of muco- and bioadhesion: tethered structures and site-specific surfaces", J. Control Release, 65(1-2):63-71 (2000).
Jokerst, et al., "Nanoparticle PEGylation for imaging and therapy", Nanomedicine (Lond), 6(4):715-728 (2011).
Knauf, et al., "Relationship of effective molecular size to systemic clearance in rats of recombinant interleukin-2 chemically modified with water-soluble polymers", J. Biol. Chem., 263(29):15064-15070 (1988).
Lai, et al., "Rapid transport of large polymeric nanoparticles in fresh undiluted human mucus", Proc. Natl. Acad. Sci. U.S.A., 104(5):1482-1487 (2007).
Lai, et al., "Mucus-penetrating nanoparticles for drug and gene delivery to mucosal tissues", Adv. Drug Deliv. Rev., 61(2):158-171 (2009).
Maisel, et al., "Effect of surface chemistry on nanoparticle interaction with gastrointestinal mucus and distribution in the gastrointestinal tract following orla and rectal administration in the mouse", J. Control. Release, 197:48-57 (2015).
Maisel, et al., "Enema ion compositions for enhancing colorectal drug delivery", J. Control. Release, 209:280-287 (2015).
Martini, et al., "The bioadhesive properties of a triblock copolymer of ε-caprolactone and ethylene oxide", Int. J. Pharm., 113(2):223-229 (1995).
Monfardini, et al., "Stabilization of substances in circulation", Bioconj. Chem., 9(4):418-450 (1998).
Nance, et al., "A dense poly(ethylene glycol) coating improves penetration of large polymeric nanoparticles within brain tissue", Sci. Transl. Med., 4(149):149ra119 (2012).
Olmsted, et al., "Diffusion of macromolecules and virus-like particles in human cervical mucus", Biophys. J., 81(4):1930-1937 (2001).
Owens, et al, "Opsonization, biodistribution, and pharmacokinetics of polymeric nanoparticles", Int. J. Pharm., 307(1):93-102 (2006).
Peppas, et al., "Hydrogels as mucoadhesive and bioadhesive materials: a review", Biomaterials, 17(16):1553-1561 (1996).
Peppas, et al., "Molecular calculations of poly(ethylene glycol) transport across a swollen poly(acrylic acid)/mucin interface", J. Biomater. Sci. Polym. Ed., 9(6):535-542 (1998).
Peppas, et al., "Nanoscale technology of mucoadhesive interactions", Adv. Drug. Deliv. Rev., 56(11):1675-1687 (2004).
Peppas, et al., "Molecular aspects of mucoadhesive carrier development for drug delivery and improved absorption", J. Biomater. Sci. Polym. Ed., 20(1):1-20 (2009).
Sahlin, et al., "Enhanced hydrogel adhesion by polymer interdiffusion: use of linear poly(ethylene glycol) as an adhesion promoter", J. Biomater. Sci. Polym. Ed., 8(6):421-436 (1997).
Schuster, et al., "Nanoparticle diffusion in respiratory mucus from humans without lung disease", Biomaterials, 34(13):3439-3446 (2013).

(56) References Cited

OTHER PUBLICATIONS

Serra, et al., "Design of poly(ethylene glycol)-tethered copolymers as novel mucoadhesive drug delivery systems", Eur. J. Pharm. Biopharm., 63(1):11-18 (2006).

Smart, et al., "The basic and underlying mechanisms of mucoadhesion", Adv. Drug Deliv. Rev., 57(11):1556-1568 (2005).

Smith, "The structure of the human vaginal mucosa in relation to the menstrual cycle and to pregnancy", Am. J. Anat., 54(1):27-85 (1934).

Suh, et al., "Real-time multiple-particle tracking: applications to drug and gene delivery", Adv. Drug. Deliv. Rev., 57(1):63-78 (2005).

Suk, et al., "The penetration of fresh undiluted sputum expectorated by cystic fibrosis patients by non-adhesive polymer nanoparticles", Biomaterials, 30(13):2591-2597 (2009).

Suk, et al., "Lung gene therapy with highly compacted DNA nanoparticles that overcome the mucus barrier", J. Control Release, 178:8-17 (2014).

Tang, et al., "Biodegradable polymer nanoparticles that rapidly penetrate the human mucus barrier", Proc. Natl. Acad. Sci. U.S.A., 106(46):19268-19273 (2009).

Wang, et al., "Addressing the PEG mucoadhesivity paradox to engineer nanoparticles that "slip" through the human mucus barrier", Angew Chem. Int. Ed. Engl., 47(50):9726-9729 (2008).

Xu, et al., "Scalable method to produce biodegradable nanoparticles that rapidly penetrate human mucus", J. Control. Release, 170(2):279-286 (2013).

Xu, et al. "Impacts of surface polyethylene glycol (PEG) density on biodegradable nanoparticle transport in mucus ex vivo and distribution in vivo", ACS Nano, 9(9):9217-9227 (2015).

Yamaoka, et al., "Distribution and tissue uptake of poly(ethylene glycol) with different molecular weights after intravenous administration to mice", J. Pharm. Sci., 83(4):601-606 (1994).

Yang, et al., "Evading immune cell uptake and clearance requires PEG grafting at densities substantially exceeding the minimum for brush conformation", Mol. Pharm., 11(4):1250-1258 (2014).

Yang, et al., "Vaginal delivery of paclitaxel via nanoparticles with non-mucoadhesive surfaces suppresses cervical tumor growth", Adv. Healthc. Mater., 3(7):1044-1052 (2014).

\* cited by examiner

PS
PS-PEG$_{MES}$
FIG. 3A
FIG. 3B
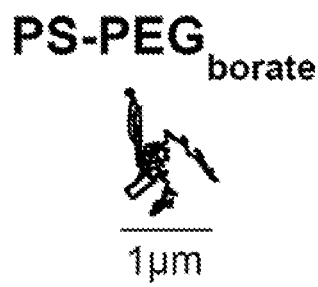
PS-PEG$_{borate}$
1μm
FIG. 3C
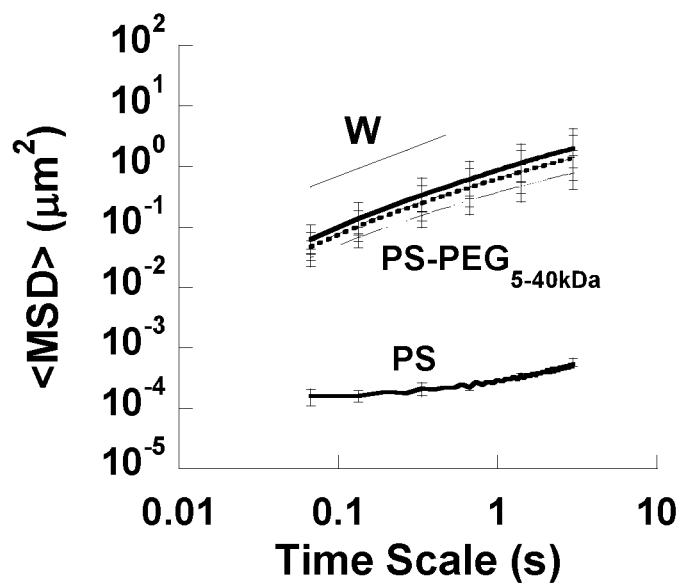
FIG. 4

PS
.
FIG. 5A
PS-PEG$_{5kDa}$
FIG. 5B
PS-PEG$_{10kDa}$
FIG. 5C
PS-PEG$_{20kDa}$
FIG. 5D
PS-PEG$_{40kDa}$
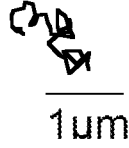
1um
FIG. 5E

PS
.
FIG. 7A
PS-PEG$_{5kDa}$
FIG. 7B
PS-PEG$_{10kDa}$
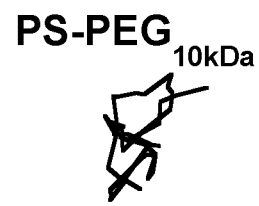
FIG. 7C
PS-PEG$_{20kDa}$
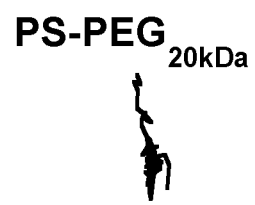
FIG. 7D
PS-PEG$_{40kDa}$
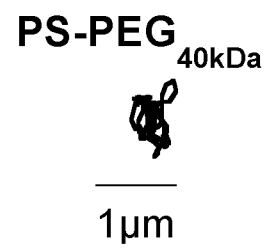
1μm
FIG. 7E

MUCUS PENETRATING PARTICLES WITH HIGH MOLECULAR WEIGHT AND DENSE COATINGS

CROSS-REFERENCE TO RELATED APPLICATIONS

This application is a National Phase application of PCT/US2016/059661, filed Oct. 31, 2016, entitled "MUCUS PENETRATING PARTICLES WITH HIGH MOLECULAR WEIGHT AND DENSE COATINGS", which claims benefit of and priority to U.S. Provisional Application No. 62/248,432, filed on Oct. 30, 2015, which are hereby incorporated herein by reference in their entirety.

STATEMENT OF FEDERALLY SPONSORED RESEARCH AND DEVELOPMENT

This invention was made with Government Support under Agreements R01HD062844, 5R21/R33AI079740, 5R21/R33AI094519 and U19AI133127 by the National Institutes of Health. The Government has certain rights in the invention.

FIELD OF THE INVENTION

This invention is in the field of nanoparticles, particularly nanoparticles densely coated with high molecular weight polymers to enable rapid penetration of mucus, and methods of making and using thereof.

BACKGROUND OF THE INVENTION

Localized delivery of therapeutics via biodegradable nanoparticles often provides advantages over systemic drug administration, including reduced systemic side effects and controlled drug levels at target sites. However, controlled drug delivery at mucosal surfaces is generally limited by the presence of the protective mucus layer.

Mucus, the first line of defense covering all mucosal surfaces, is an adhesive, viscoelastic gel that effectively prevents particulates from reaching the epithelial surface if they are larger than, and/or adhere to, the mucus mesh (Cone, Mucosal Immunology, 3rd Edition 2005, 49-72; Cone, Adv Drug Deliv Rev, 2009, 61, 75-85; Lai et al., Proc Natl Acad Sci USA, 2007, 104, 1482-1487; Olmsted et al., Biophys J, 2001, 81, 1930-1937; Ensign, Sci Transl Med, 2012, 4, 138ra179).

The mucosa consists of an epithelium, formed of one or more layers of epithelial cells and an underlying lamina propria of loose connective tissue. The mucous membranes ensure that the underlying lamina propria of connective tissue remains moist by secreting mucus. Mucus efficiently traps foreign particles and particulates by both steric and adhesive mechanisms, facilitating rapid clearance and hindering drug delivery.

The adhesion of drug particles and/or delivery vehicles to mucus can significantly decrease the efficiency of drug delivery. For example, most therapeutics delivered locally to mucosal surfaces suffer from poor retention and distribution as a result of mucus turnover. Thus, "mucoadhesion" has been shown to result in limited distribution of drugs delivered directly to the mucosa over vaginal, lung, and colorectal tissues (Ensign, Sci Transl Med, 2012, 4, 138ra179; Ensign et al., Biomaterials, 2013, 34, 6922-6929; Suk et al., J Control Release, 2014, 178, 8-17; Maisel et al., J Control Release, 2015, 10, 197, 48-57, Epub 2014 Nov. 4), which severely limits the efficacy of these drugs.

For drug or gene delivery applications, therapeutic particles must be able to achieve uniform distribution over the mucosal surface of interest and cross the mucus barrier efficiently to avoid rapid mucus clearance, ensuring effective delivery of their therapeutic payloads to underlying cells (das Neves J & Bahia M F, Int J Pharm, 2006, 318, 1-14; Lai et al., Adv Drug Deliver Rev, 2009, 61, 158-171; Ensign et al., Sc. Transl Med, 2012, 4, 138ra179, 1-10; Eyles et al., J Pharm Pharmacol, 1995, 47, 561-565).

Many factors are known to contribute to the mucoadhesive characteristics of nanoparticles (Lai et al., Proc Natl Acad Sci USA, 2007, 104, 1482-1487; Ensign, Sci Transl Med, 2012, 4, 138ra179). Typically, positively charged surfaces, and/or uncoated hydrophobic surfaces are considered to be highly mucoadhesive. PEG has been used to enhance mucoadhesion (Peppas, J Biomater Sci Polym Ed, 1998, 9, 535-542; Peppas et al., Adv Drug Deliv Rev, 2004, 56, 1675-1687; Peppas et al., Biomaterials, 1996, 17, 1553-1561; Peppas et al., Biomater Sci Polym Ed, 2009, 20, 1-20; Sahlin et al., J Biomater Sci Polym Ed, 1997, 8, 421-436; Huang et al., J Coontro Release, 2000, 65, 63-71; Smart et al., Adv Drug Deliv Rev, 2005, 57, 1556-1568; Serra et al., Eur J Pharm Biopharm, 2006, 63, 11-18). High-molecular weight PEG has been described as acting as a mucoadhesive "glue" that interpenetrates and entangles with mucin fibers (Peppas, J Biomater Sci Polym Ed, 1998, 9, 535-542; Peppas & Sahlin, Biomaterials, 1996, 17, 1553-1561) or forms hydrogen bonds to the carbohydrate regions of the mucin fibers (Deascentiis et al., J Control Release, 1995, 33, 197-201; Peppas, J Biomater Sci Polym Ed, 1998, 9, 535-542; Peppas & Huang, Adv Drug Deliv Rev, 2004, 56, 1675-1687; Peppas & Sahlin, Biomaterials, 1996, 17, 1553-1561; Peppas et al., J Biomater Sci Polym Ed, 2009, 20, 1-20; Martini et al., International Journal of Pharmaceutics, 1995, 113, 223-229; Sahlin & Peppas, J Biomater Sci Polym Ed, 1997, 8, 421-436; Huang et al., J Control Release, 2000, 65, 63-71). PEG of a molecular weight as high as 10 kDa has been reported to have inconsistent influences on the mucus penetration of coated particles. For example, 10 kDa PEG of a comparable coating density as 2 kDa PEG (e.g., PEG 2 kDa) either caused mucoadhesion (Wang et al., Angew Chem Int Ed Engl, 2008, 47, 9726-9729) or exhibited similar mucoadhesive capacity as non-coated particles (Deascentiis et al., J Control Release, 1995, 33, 197-201). In another example, PLGA-PEG nanoparticles formed using an emulsion method allowed PEG to partition to the particle surface during the slow hardening process, resulting in a sufficiently high surface density for up to 10 kDa PEG for mucus penetrating coatings (Xu et al., J Control Release, 2013, 170, 279-286).

Other studies established that nanoparticles densely coated with low-molecular weight hydrophilic polymers, such PEG 1 kD, are able to penetrate mucus barriers to reach and uniformly coat epithelial surfaces (Lai et al., Proc Natl Acad Sci USA, 2007, 104, 1482-1487; Ensign, Sci Transl Med, 2012, 4, 138ra179; Suk et al., J Control Release, 2014, 178, 8-17; Maisel et al., J Control Release, 2015, 10, 197, 48-57, Epub 2014 Nov. 4). In addition, these mucus penetrating nanoparticles (MPP) are retained for longer periods of time in the cervicovaginal and respiratory tracts compared to mucoadhesive particulates (Ensign, Sci Transl Med, 2012, 4, 138ra179; Suk et al., J Control Release, 2014, 178, 8-17), indicating that MPP may be more suitable for distributing drugs to the entire epithelial surface and providing prolonged drug retention.

There exists a need for new methods of preparing mucus-penetrating particles which can encapsulate a wide range of drugs into the nanoparticles without a decrease in the mucus penetrating properties as described above. There is a similar need for formulations which are administered via injection.

Therefore, it is an object of the invention to provide methods of preparing particles, and the resulting particles, which can encapsulate a wide range of drugs into the biodegradable nanoparticles without a decrease in the mucus penetrating properties.

It is another object of the invention to provide particles, such as nanoparticles and microparticles, with high drug loading and a dense coating of a surface-altering material to provide effective drug delivery via a variety of routes of administration including via mucosal surfaces.

SUMMARY OF THE INVENTION

Mucus penetrating particles (MPPs) include one or more core polymers, one or more therapeutic, prophylactic and/or diagnostic agents; and one or more surface modifying agents. The surface modifying agents coat the surface of the particle in a sufficient density to enhance the diffusion of the modified nanoparticles through mucus, relative to equivalent nanoparticles that are not surface modified. Nanoparticles can be sufficiently densely coated with poly(ethylene glycol) (PEG) with a molecular weight of from 10,000 Daltons to 40,000 Daltons or greater, to cause the nanoparticles to rapidly diffuse through mucus ex vivo and in vivo.

There is a minimal PEG packing density threshold at the surface of nanoparticles that must be exceeded to effectively shield the particle surface from interactions with mucus. There is a narrow margin between where the surface packing density is sufficient or insufficient. In some embodiments, the surface modifying agent is poly(ethylene glycol) having a molecular weight from greater than about 5 kDa to about 100 kDa, inclusive, preferably from about 10 kDa to about 40 kDa, inclusive, more preferably about 20 kDa. The mucus penetrating nanoparticles are coated with a surface modifying agent at a density that is sufficient to enable diffusion through mucus even with PEG having molecular weights greater than 5-10 kD. In some embodiments the surface density of the surface-modifying agent is measured by $^1$H NMR. Typically, when PEG is the surface modifying agent, MPP are coated with a surface density from about 0.1 to about 100 molecules/100 nm$^2$, preferably from about 0.5 to about 50 molecules/100 nm$^2$, more preferably from about 0.9 to about 45 molecules/100 nm$^2$.

In some embodiments, surface packing density is measured as a function of the formula:

$$\Gamma/SA = \text{Surface packing density}$$

where $\Gamma$ is the total surface area coverage that can be provided by the PEG molecules assuming PEG conformation on the particle surface is unconstrained, and SA is the total nanoparticle surface area. When PEG is the surface modifying agent, MPP are coated with surface packing density of 1.5 or greater. In some embodiments, the surface modifying agents are in an amount effective to make the surface charge of the MPP neutral or essentially neutral in physiological fluids. For example, in some embodiments, the nanoparticles have a zeta-potential of between about −10 mV and 10 mV, inclusive, preferably between about −5 mV and 5 mV, inclusive, most preferably between about −2 mV and 2 mV, inclusive.

The MPPs typically have a hydrodynamic diameter of between about 50 nm and 500 nm, inclusive, preferably between about 60 nm and 300 nm, inclusive.

In some embodiments, the nanoparticles include a pharmaceutically acceptable excipient for administration into or onto the body. Exemplary pharmaceutical compositions are formulated for administration by enteral, parenteral, or topical administration.

Methods of making mucus penetrating nanoparticles are also provided. The methods include the steps of suspending core polymer nanoparticles in borate buffer, pH 7.4 to form an incubation mixture; adding methoxy-poly(ethylene glycol)-amine to the incubation mixture; covalently coupling the methoxy-poly(ethylene glycol)-amine to the core polymer nanoparticles; and isolating the mucus penetrating nanoparticles from the mixture.

Methods of using MPPs to deliver one or more therapeutic, prophylactic, and/or diagnostic agents to a subject in need thereof are also provided. The methods include administering to the subject an effective amount of MPPs to achieve a desired biological effect. For example, in some embodiments, the MPPs are in an amount effective to diagnose, prevent or treat one or more symptoms of a disease or disorder. Generally, MPP are coated with the surface modifying agent at a density effective to penetrate mucus and provide uniform distribution of the particles at the mucosal epithelium of a subject. Exemplary mucosal epithelia include the vaginal epithelium, colorectal tract, ophthalmic epithelium, respiratory tract, mouth and combinations thereof. In a particular embodiment, the MPP coated with the surface modifying agent at a density effective to penetrate cervicovaginal mucus, colorectal mucus, respiratory tract mucus, or combinations thereof.

BRIEF DESCRIPTION OF THE DRAWINGS

FIGS. 3A, 3B, and 3C show representative trajectories for 3 seconds of motions of 200 nm PS (3A) and PS-PEG NPs (3B, 3C) in human cervicovaginal mucus. PS-PEG NPs are coated with 10 kDa PEG using the MES method (3B) or the borate method (3C). Data are representative of n>3 samples.

FIG. 4 shows the ensemble averaged mean-squared displacement (<MSD>) as a function of time up to 3 seconds for 200 nm PS and PS-PEG NP coated with 5 kDa, 10 kDa, 20 kDa, or 40 kDa PEG using the borate method, including the theoretical MSD of 200 nm particles in water (W).

FIGS. 5A, 5B, 5C, 5D, and 5E show representative trajectories for 3 seconds of motion of 200 nm PS (5A) and PS-PEG NPs (5B-5E) in human cervicovaginal mucus. FIGS. 5B, 5C, 5D, and 5E show PS-PEG NPs coated with 5 kDa, 10 kDa, 20 kDa, and 40 kDa PEG, respectively, using the borate method. Data are representative of n≥3 samples.

FIGS. 7A, 7B, 7C, 7D, and 7E show representative trajectories for 3 seconds of motion of 100 nm PS (7A) and PS-PEG NPs (7B-7E) in human cervicovaginal mucus. FIGS. 7B, 7C, 7D, and 7E shows PS-PEG NPs coated with 5 kDa, 10 kDa, 20 kDa, and 40 kDa PEG, respectively, using the borate method. Data are representative of n>3 samples.

DETAILED DESCRIPTION OF THE INVENTION

I. Definitions

Figure 1:
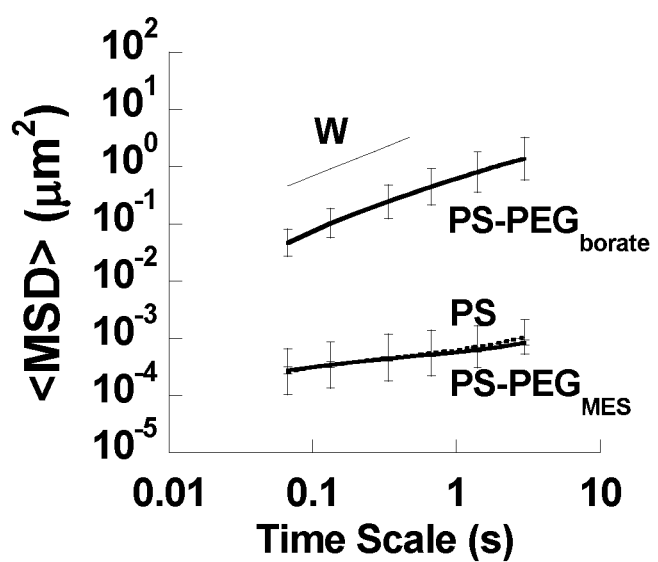
FIG. 1 shows the ensemble mean-squared displacement (<MSD>) with respect to time up to 3 seconds for 200 nm PS and PS-PEG NP coated with 10 kDa PEG using the borate or MES method, including the theoretical MSD of 200 nm nanoparticles in water (W). Data are representative of n≥3 samples.

The term "Nanoparticle" generally refers to a particle of any shape having a diameter from about 1 nm up to, but not including, about 1 micron, more preferably from about 5 nm to about 500 nm, most preferably from about 5 nm to about 100 nm. Nanoparticles having a spherical shape are generally referred to as "nanospheres".

The term "Mean particle size" generally refers to the statistical mean particle size (diameter) of the particles in a population of particles. The diameter of an essentially spherical particle may be referred to as the physical or hydrodynamic diameter. The diameter of a non-spherical particle may refer preferentially to the hydrodynamic diameter. As used, the diameter of a non-spherical particle may refer to the largest linear distance between two points on the surface of the particle. Mean particle size can be measured using methods known in the art, such as dynamic or static light scattering, Fast Protein Liquid Chromatography, etc.

The term "Mucus" refers to a viscoelastic natural substance containing primarily mucin glycoproteins and other materials, which protects epithelial surface of various organs/tissues, including respiratory, nasal, cervicovaginal, gastrointestinal, rectal, visual and auditory systems. "Sputum," as used herein, refers to highly viscoelastic mucus secretions consist of a variety of macromolecules such as DNA, actins and other cell debris released from dead cells in addition to mucin glycoproteins. "Sputum" is generally present in the pathogenic airways of patients afflicted by obstructive lung diseases, including but not limited to, asthma, COPD and CF. "CF mucus" and "CF sputum," as used herein, refer to mucus and sputum, respectively, from a patient suffering from cystic fibrosis.

The terms "incorporated" and "encapsulated" refers to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including, for example: attached to a monomer of such polymer (by covalent, ionic, or other binding interaction), physical admixture, enveloping the agent in a coating layer of polymer, incorporated into the polymer, distributed throughout the polymeric matrix, appended to the surface of the polymeric matrix (by covalent or other binding interactions), encapsulated inside the polymeric matrix, etc. The term "co-incorporation" or "co-encapsulation" refers to-the incorporation of a therapeutic agent or other material and at least one other therapeutic agent or other material in a subject composition.

The term "biocompatible" refers to one or more materials that are neither themselves toxic to the host (e.g., an animal or human), nor degrade (if the polymer degrades) at a rate that produces monomeric or oligomeric subunits or other byproducts at toxic concentrations in the host.

The term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease or disorder, and the treatment being effected.

II. Mucus-Penetrating Nanoparticles (MPPs)

The controlled delivery of drugs to mucosal surfaces is challenging because of the presence of the protective mucus layer. Mucus-penetrating particles (MPPs) show improved drug distribution, retention and efficacy at mucosal surfaces based on the discovery that it is possible to coat the particles with hydrophilic polymer having a molecular weight over 5 kD, if the surface density is sufficiently high.

A. Core Polymer

Any number of biocompatible polymers can be used to prepare the nanoparticles. In one embodiment, the biocompatible polymer(s) is biodegradable. In another embodiment, the particles are non-degradable. In other embodiments, the particles are a mixture of degradable and non-degradable particles.

Exemplary polymers include, but are not limited to, polymers prepared from lactones such as poly(caprolactone) (PCL), polyhydroxy acids and copolymers thereof such as poly(lactic acid) (PLA), poly(L-lactic acid) (PLLA), poly (glycolic acid) (PGA), poly(lactic acid-co-glycolic acid) (PLGA), poly(L-lactic acid-co-glycolic acid) (PLLGA), poly(D,L-lactide) (PDLA), poly(D,L-lactide-co-caprolactone), poly(D,L-lactide-co-caprolactone-co-glycolide), poly (D,L-lactide-co-PEO-co-D,L-lactide), poly(D,L-lactide-co-PPO-co-D,L-lactide), and blends thereof, polyalkyl cyanoacralate, polyurethanes, polyamino acids such as poly-L-lysine (PLL), poly(valeric acid), and poly-L-glutamic acid, hydroxypropyl methacrylate (HPMA), polyanhydrides, polyorthoesters, poly(ester amides), polyamides, poly(ester ethers), polycarbonates, ethylene vinyl acetate polymer (EVA), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), celluloses including derivatized celluloses such as alkyl celluloses, hydroxyalkyl celluloses, cellulose ethers, cellulose esters, nitro celluloses, hydroxypropylcellulose, and carboxymethylcellulose, polymers of acrylic acids, such as poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), polydioxanone and its copolymers, polyhydroxyalkanoates, polypropylene fumarate, polyoxymethylene, poloxamers, poly(butyric acid), trimethylene carbonate, and polyphosphazenes.

In the preferred embodiments, the polymer is an FDA approved biodegradable polymer such as a hydroxy acid (PLA, PLGA, PGA), polyanhydride or polyhydroxyalkanoate such as poly(3-butyrate) or poly(4-butyrate) or copolymer thereof.

Copolymers of the above, such as random, block, or graft copolymers, or blends of the polymers listed above can also be used. Functional groups on the polymer can be capped to alter the properties of the polymer and/or modify (e.g., decrease or increase) the reactivity of the functional group. For example, the carboxyl termini of carboxylic acid contain polymers, such as lactide- and glycolide-containing polymers, may optionally be capped, e.g., by esterification, and the hydroxyl termini may optionally be capped, e.g. by etherification or esterification.

The weight average molecular weight can vary for a given polymer but is generally from about 1 kD to 1,000 kD, 1 kD to 500 kD, 1 kD to 250 kD, 10 kD to 100 kD, 5 kD to 100 kD, 5 kD to 75 kD, 5 kD to 50 kD, or greater than 5 kD to 25 kD.

B. Surface Modifying Agents

The nanoparticles are preferably coated with or formed with a surface of one or more surface altering agents or materials. The term "Surface-altering agent" refers to an agent or material which modifies one or more properties of the surface for the particles, including, but not limited to, hydrophilicity (e.g., makes the particles more or less hydrophilic), surface charge (e.g., makes the surface neutral or near neutral or more negative or positive), and/or enhances transport in or through bodily fluids and/or tissues, such as mucus. The most preferred material is a polyalkylene oxide such as poly(ethylene glycol) (PEG).

In preferred embodiments, the particles are coated with or contain poly(ethylene glycol) (PEG), such as PEG with a molecular weight of at least 10,000 daltons.

PEG (CAS number 25322-68-3) is a linear polyether diol with many useful properties, such as biocompatibility (Powell G M. Polyethylene glycol. In: Davidson R L, editor. Handbook of water soluble gums and resins. McGraw-Hill: 1980. pp. 18-31), solubility in aqueous and organic media, lack of toxicity, very low immunogenicity and antigenicity (Dreborg et al., Crit Rev Ther Drug Carrier Syst, 1990, 315-65), and good excretion kinetics (Yamaoka et al., J Pharm Sci, 1994, 83:601-6). For example, poly-(ethylene glycol) has been used to derivatize therapeutic proteins and peptides, increasing drug stability and solubility, lowering toxicity, increasing half-life (Caliceti et al., Adv Drug Del Rev, 2003, 55, 1261-77), decreasing clearance and immunogenicity. These benefits have been particularly observed using branched PEG in the derivatization (Monfardini et al., Bioconj Chem, 1998, 9, 418-50).

The molecular weight and structure of PEG molecules can be modulated for specific purposes. In preferred embodiments, the PEG has a molecular weight of 10,000 daltons (PEG-10 kDa) or greater.

Copolymers of high molecular weight PEG or derivatives thereof with any of the core polymers described above may be used to make the polymeric particles. In certain embodiments, the PEG or derivatives may be located in the interior positions of the copolymer. Preferably, the PEG or derivatives may locate near or at the terminal positions of the copolymer. For example, one or more of the polymers above can be terminated with a block of polyethylene glycol or polyethylene oxide (PLURONIC®), block copolymers of polyethylene glycol and polyethylene oxide.

In some embodiments, the core polymer is a blend of pegylated polymer and non-pegylated polymer, wherein the base polymer is the same (e.g., polystyrene (PS) and PS-PEG) or different (e.g., PS-PEG and poly(lactic acid)).

High molecular weight PEG can be applied as coating onto the surface of the particles. In certain embodiments, nanoparticles are formed under conditions that allow regions of PEG to phase separate or otherwise locate to the surface of the particles. The surface-localized PEG regions alone may perform the function of, or include, the surface-altering agent. In other embodiments, the particles are prepared from one or more polymers terminated with blocks of polyethylene glycol as the surface-altering material. The PEG can be in the form of blocks covalently bound (e.g., in the interior or at one or both terminals) to the core polymer used to form the particles. In particular embodiments, the particles are formed from block copolymers containing PEG. In more particular embodiments, the particles are prepared from block copolymers containing PEG, wherein PEG is covalently bound to the terminal of the base polymer.

Representative PEG molecular weights for formulating into mucus penetrating particles include 10,000 daltons (10 kDa), 15 kDa, 20 kDa, 30 kDa, 40 kDa, 50 kDa, 60 kDa, 100 kDa, 200 kDa, 500 kDa, and 1 MDa and all values within the range of 10 kDa to 1 MDa. In some embodiments, the PEG has a molecular weight of 10 kDa, or greater than 10 kDa, such as 20 kDa-100 kDa inclusive, preferably 20 kDa-40 kDa. PEG of any given molecular weight may vary in other characteristics such as length, density, and branching.

Other polymers that may be useful include poly(vinyl pyrrolidone), and poly(acryl amide).

Density of Surface Modifying Agents

The density of surface altering agents is a key parameter in determining the ability of nanoparticles to penetrate mucus and influences the successful delivery of active agents to the mucosal epithelium in-vivo.

Different techniques can be employed to measure the surface PEG density on nanoparticles, including those that directly measure changes to physiochemical properties of nanoparticles, such as surface charge and hydrodynamic diameter. Typically, the methods to determine surface density provide quantitative information about the number of PEG chains per $nm^2$ of the particle surface.

Thermogravimetric analysis (TGA) can be used to calculate PEG content. Typically, TGA is limited to inorganic materials and requires the use of relatively large quantity of samples.

Reaction of dye and reagents (such as fluorescence dye) to functional PEG can be used for PEG quantification. In these methods, the un-reacted PEG molecules with functional groups (such as —SH, —$NH_2$, etc.) are quantified by fluorescent assay or colorimetric quantification after the reaction with certain reagents, and the surface PEG density is determined by subtracting the un-reacted PEG portion in supernatant. However, these methods are limited to surface PEGylation and functional PEG. Similar methods used to quantify surface PEG density on PRINT nanoparticles by the measurement of signal of un-reacted fluorescein-PEG in supernatant are limited to surface modification of nanoparticles with PEG. These quantitative assays are not suitable for determining the PEG density on biodegradable nanoparticles prepared from PEG-containing block copolymers, such as the widely used poly(lactic-co-glycolic acid)-poly (ethylene glycol) (PLGA-PEG) and poly(lactic acid)-poly (ethylene glycol) (PLA-PEG).

In other embodiments, nuclear magnetic resonance (NMR) is used to assess the surface PEG density on PEG-containing polymeric nanoparticles, both qualitatively and quantitatively (PEG peak typically observed ~3.65 ppm).

When nanoparticles are dispersed within the NMR solvent $D_2O$, only the surface PEG, not the PEG embedded within the core, can be directly detected by NMR. Therefore, NMR provides a means for directly measure the surface density of PEG.

In some embodiments, PEG surface density is controlled by preparing the particles from a mixture of pegylated and non-pegylated particles. For example, the surface density of PEG on PLGA nanoparticles can be precisely controlled by preparing particles from a mixture of poly(lactic-co-glycolic acid) and poly(ethylene glycol) (PLGA-PEG). Typically, quantitative $^1H$ NMR is used to measure the surface PEG density on nanoparticles.

Previously, it was determined that low-density coating of low-molecular weight PEG (e.g., PEG 2 kDa) caused mucoadhesion compared to high-density coating of the same PEG, and that high-molecular weight PEG (e.g., PEG 10 kDa) of a comparable density of coating to low-molecular weight PEG (e.g., PEG 2 kDa) caused mucoadhesion (Wang et al., Angew Chem Int Ed Engl, 2008, 47, 9726-9729). The high molecular weight PEG mucus-penetrating nanoparticles include a surface modifying agent at a density that is sufficient to penetrate the mucus barrier described herein is mucus penetrating despite the higher molecular weight.

It has been established that the density of surface coating, as opposed to molecular weight of the coating agent per se, mediates the ability of nanoparticles to penetrate mucus.

Surface packing density is expressed as the total unconstrained PEG surface area coverage ($\Gamma$) divided by the total particle surface area (SA):

$$(\Gamma/SA) = \text{Packing Density}$$

In some embodiments there is a minimal packing density threshold that must be exceeded to effectively shield the nanoparticle surface from interactions with mucus. In certain embodiments, there is a narrow margin between where the packing density of the coating is sufficient or insufficient.

In some embodiments, a surface density value, determined according to the above formula, of 1.3 or less than 1.3 gives rise to adhesion in cervicovaginal mucus (CVM). Therefore, in some embodiments the mucus penetrating nanoparticles have a PEG surface density ($\Gamma/SA$) $\geq 1.5$, for example, 1.6, 1.7, 1.8, 1.9, 2.0, 2.1, 2.2, 2.3, 2.4, 2.5, or greater than 2.5.

The threshold surface packing density value at which mucus penetration occurs can be determined experimentally, for example, by analysis of the ensemble averaged mean square displacement (MSD) in mucus, as compared to the theoretical MSD for similarly sized particles in water ($MSD_W$).

Typically, the number of PEG molecules per 100 nm$^2$ of particle surface area decreases as the PEG MW increases, which can be attributed to the increased amount of space occupied by each PEG chain as the MW increases; for example, the area occupied by one unconstrained 5 kDa PEG chain is ~23 nm$^2$, compared to ~180 nm$^2$ for unconstrained 40 kDa PEG molecules.

The dense coating of PEG on biodegradable nanoparticles allows rapid penetration through mucus because of the greatly reduced adhesive interaction between mucus constituents and nanoparticles. As demonstrated in the Examples, multiple particle tracking in human mucus and the study of mucin binding and tissue distribution in mouse vagina revealed that there exists a PEG density threshold. In some embodiments, for polystyrene (PS) nanoparticles conjugated with PEG having a molecular weight of 10,000 daltons, the surface packing threshold is approximately 1-5 PEG chains/100 nm$^2$, inclusive, or greater to be effective in penetrating mucus.

The surface packing density threshold can vary depending on a variety of factors including the core polymer used to prepare the particles, particle size, and/or molecular weight of PEG.

The density of the coating can be varied based on a variety of factors including the surface altering material and the composition of the particle. In one embodiment, the density of the surface altering material, such as PEG, as measured by $^1H$ NMR is at least, 0.1, 0.2, 0.5, 0.8, 0.9, 1.0, 1.2, 1.5, 1.8, 2.0, 2.9, 3.0, 3.3, 4.0, 4.4, 5.0, or more than 5.0 chains per 100 nm$^2$. The range above is inclusive of all values from 0.1 to 100 units per nm$^2$, inclusive.

In particular embodiments, the density of the surface altering material, such as PEG, is from about 0.001 to about 2 chains/nm$^2$, from about 0.01 to about 0.1 chains/nm$^2$, from about 0.05 to about 0.5 chains/nm$^2$, from about 0.1 to about 0.2 chains/nm$^2$, or from about 0.15 to about 0.2 chains/nm$^2$. The concentration of the surface altering material, such as PEG, can also be varied. In some embodiments, the target concentration of the surface altering material, such as PEG, is at least 0.5, 1, 2, 3, 4, 5, 6, 7, 8, 9, 10, 11, 12, 13, 14, 15, 16, 17, 18, 19, 20, 21, 22, 23, 24, or 25% or higher. The range above is inclusive of all values from 0.5% to 25%. In another embodiment, the concentration of the surface altering material, such as PEG, in the particle is at least 0.5, 1, 2, 3, 4, 5, 6, 7, 8, 9, 10, 11, 12, 13, 14, 15, 16, 17, 18, 19, 20, 21, 22, 23, 24, or 25%. The range above is inclusive of all values from 0.5% to 25%. In still other embodiments, the surface altering material content (e.g., PEG) on the surface of the particles is at least 0.5, 1, 2, 3, 4, 5, 6, 7, 8, 9, 10, 11, 12, 13, 14, 15, 16, 17, 18, 19, 20, 21, 22, 23, 24, or 25%. The range above is inclusive of all values from 0.5% to 25%.

In particular embodiments, the density of the surface-altering material (e.g., PEG) is such that the surface-altering material (e.g., PEG) adopts an extended brush configuration.

In other embodiments, the mass of the surface-altering moiety is at least 1/10,000, 1/7500, 1/5000, 1/4000, 1/3400, 1/2500, 1/2000, 1/1500, 1/1000, 1/750, 1/500, 1/250, 1/200, 1/150, 1/100, 1/75, 1/50, 1/25, 1/20, 1/5, 1/2, or 9/10 of the mass of the particle. The range above is inclusive of all values from 1/10,000 to 9/10.

Typically, the hydrodynamic diameter of the nanoparticles after PEGylation increases as the PEG MW increases; for example, dense packing of the PEG chains causes elongation, so higher MW PEG chains would create a thicker corona.

C. Therapeutic, Prophylactic, Nutraceutical and/or Diagnostic Agents

Mucus penetrating nanoparticles (MPPs) can be formulated with one or more active agents for delivery to the mucosal surface. Typically, MPP include one or more therapeutic, prophylactic, nutraceutical and/or diagnostic agents.

For those embodiments where the one or more therapeutic, prophylactic, and/or diagnostic agents are encapsulated within a polymeric nanoparticle and/or associated with the surface of the nanoparticle, the percent drug loading is from about 1% to about 80%, from about 1% to about 50%, preferably from about 1% to about 40% by weight, more preferably from about 1% to about 20% by weight, most preferably from about 1% to about 10% by weight. The ranges above are inclusive of all values from 1% to 80%. For those embodiments where the agent is associated with the surface of the particle, the percent loading may be higher since the amount of drug is not limited by the methods of encapsulation. In some embodiments, the agent to be delivered may be encapsulated within a nanoparticle and associated with the surface of the particle.

Exemplary active agents are discussed in more detail, below.

In some embodiments, the particles have encapsulated therein, dispersed therein, and/or covalently or non-covalently associate with the surface one or more therapeutic agents. The therapeutic agent can be a small molecule, protein or peptide, sugar or polysaccharide, nucleic acid molecule and/or lipid.

Exemplary classes of small molecule therapeutic agents include, but are not limited to, analgesics, anti-inflammatory drugs, antipyretics, antidepressants, antiepileptics, antipsychotic agents, neuroprotective agents, anti-proliferatives, such as anti-cancer agent, anti-infectious agents, such as antibacterial agents and antifungal agents, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics.

Exemplary prophylactic agents include vaccine antigens.

In some embodiments, the agent is one or more nucleic acids. The nucleic acid can alter, correct, or replace an endogenous nucleic acid sequence. The nucleic acid is used to treat cancers, correct defects in genes in other pulmonary diseases and metabolic diseases.

Exemplary nucleic acids include DNA, RNA, chemically modified nucleic acids, and combinations thereof. Methods for increasing stability of nucleic acid half-life and resistance to enzymatic cleavage are known in the art.

Exemplary diagnostic materials include paramagnetic molecules, fluorescent compounds, magnetic molecules, and radionuclides. Suitable diagnostic agents include, but are not limited to, x-ray imaging agents and contrast media. Radionuclides also can be used as imaging agents. Examples of other suitable contrast agents include gases or gas emitting compounds, which are radioopaque. Nanoparticles can further include agents useful for determining the location of administered particles. Agents useful for this purpose include fluorescent tags, radionuclides and contrast agents.

For those embodiments where the one or more therapeutic, prophylactic, and/or diagnostic agents are encapsulated within a polymeric nanoparticle and/or associated with the surface of the nanoparticle, the percent drug loading is from about 1% to about 80%, from about 1% to about 50%, preferably from about 1% to about 40% by weight, more preferably from about 1% to about 20% by weight, most preferably from about 1% to about 10% by weight. The ranges above are inclusive of all values from 1% to 80%. For those embodiments where the agent is associated with the surface of the particle, the percent loading may be higher since the amount of drug is not limited by the methods of encapsulation. In some embodiments, the agent to be delivered may be encapsulated within a nanoparticle and associated with the surface of the particle. Nutraceuticals can also be incorporated. These may be vitamins, supplements such as calcium or biotin, or natural ingredients such as plant extracts or phytohormones.

D. Properties of the Particles

Particle size, zeta-potential ($\zeta$-potential), PEG surface density (area covered by PEG/total surface area, or $\Gamma$/SA), are all factors that can influence the ability of the nanoparticles move in and penetrate through mucus. Comparison of the ensemble averaged MSD in mucus (<MSD>) to the theoretical MSD of similarly sized particles in water ($MSD_w$) can be used to indicate how much slower the nanoparticles move in mucus, MSDw/<MSD>.

1. Surface Charge and Particle Size

In order to facilitate their diffusion through mucus, the nanoparticles typically possess a near neutral surface charge. In certain embodiments, the nanoparticle possess $\zeta$-potential of between about 10 mV and about −10 My inclusive, preferably between about 5 mV and about −5 mV, more preferably between about 3 mV and about −3 mV, most preferably between about 2 mV and about −2 mV.

Typically, the surface altering material (e.g., PEG) must be present in sufficient density to form a corona which shields the positively or negatively charged core polymer, resulting in an effectively neutral surface.

While the particles described herein are referred to as nanoparticles, typically having an average diameter in the range of 1 nm up to, but not including, about 1 micron, more preferably from about 50 nm to about 900 nm, most preferably from about 60 nm to about 500 nm. In certain embodiments, the average diameter of the particles is form about 60 nm to about 300 nm. However, particles can be prepared that are sized in the micron-range. The conditions and/or materials used to prepare the particles can be varied to vary the size of the particles.

In certain embodiments, the nanoparticles retain their particle size and $\zeta$-potential after nebulization or storage for at least 1 month, more preferably at least 2 months, most preferably at least 3 months at 4° C.

In an exemplary embodiment, 200 nm polystyrene nanoparticles (PS NP) coated with 5-40 kDa PEG (PS-PEG-NP) rapidly penetrated cervicovaginal mucus (CVM), as indicated by the averaged mean squared displacement (<MSD>) values measured, and exhibited diffusive behavior, in stark contrast to the uncoated PS NP (See Table 1).

III. Pharmaceutical Compositions

In some embodiments, mucus penetrating nanoparticles (MPP) are formulated into pharmaceutically acceptable compositions for administration onto or into the body.

The formulations described herein contain an effective amount of nanoparticles ("MPPs") in a pharmaceutical carrier appropriate for administration to a mucosal surface.

A. Solutions, Emulsions, and Gels

The particles can be administered in a pharmaceutically acceptable formulation, such as sterile saline, phosphate buffered saline or a hypotonic solution that enhances uptake. In some embodiments, the pharmaceutical carrier is adjusted to have a certain desired tonicity. For example, in certain embodiments the pharmaceutical carrier is adjusted to be hypotonic. One skilled in the art can routinely adjust tonicity of pharmaceutical carriers, once the desired tissue to be treated is identified, based on the preferred tonicity ranges described herein.

Tonicity is the 'effective osmolality' and is equal to the sum of the concentrations of the solutes which have the capacity to exert an osmotic force across the membrane. A number of different materials can be used to adjust tonicity. For example, the USP 29-NF 24 lists five excipients classified as "tonicity" agents, including dextrose, glycerin; potassium chloride; mannitol; and sodium chloride See, for example, United States Pharmacopeial Convention, Inc. *United States Pharmacopeia 29—National Formulary* 24. Rockville Md.: U.S. Pharmacopeial Convention, Inc.; 2005:

3261; Day, A. Dextrose. In: Rowe R C, Sheskey P J and Owen S C, eds. *Handbook of Pharmaceutical Excipients*. 5th ed. Washington D.C.: American Pharmaceutical Association; 2005: 231-233; Price J C. Glycerin. In: Rowe R C, Sheskey P J and Owen S C, eds. *Handbook of Pharmaceutical Excipients*. 5th ed. Washington D.C.: American Pharmaceutical Association; 2005: 301-303; Price J C. Glycerin. In: Rowe R C, Sheskey P J and Owen S C, eds. *Handbook of Pharmaceutical Excipients*. 5th ed. Washington D.C.: American Pharmaceutical Association; 2005: 301-303; Armstrong N A. Mannitol. In: Rowe R C, Sheskey P J and Owen S C, eds. *Handbook of Pharmaceutical Excipients*. 5th ed. Washington D.C.: American Pharmaceutical Association; 2005: 449-453; Owen S C. Sodium Chloride. In: Rowe R C, Sheskey P J and Owen S C, eds. Handbook of Pharmaceutical Excipients. 5th ed. Washington D.C.: American Pharmaceutical Association; 2005: 671-674. Mannitol is an example of a GRAS listed ingredient accepted for use as a food additive in Europe, included in the FDA Inactive Ingredients Database (IP, IM, IV, and SC injections; infusions; buccal, oral and sublingual tablets, powders and capsules; ophthalmic preparations; topical solutions), included in non-parenteral and parenteral medicines licensed in the UK and included in the Canadian Natural Health Products Ingredients Database. A 5.07% w/v aqueous solution is iso-osmotic with serum.

Minimally hypotonic formulations, preferably ranging from 20-220 mOsm/kg, provide rapid and uniform delivery of MPP to the entire vaginal surface, with minimal risk of epithelial toxicity. There is a higher osmolality in the colon, such that vehicles with an osmolality above that of blood plasma (generally considered isotonic at ~300 mOsm/kg), leads to improvements in distribution in the colon. The range for improved colon distribution with a hypotonic vehicle in the colon is ~20 mOsm/kg-450 mOsm/kg if a major fraction of the solutes in the formulation consists of $Na^+$ ions, since these will be actively taken up (absorbed) by the epithelium, thus making the formulation effectively hypotonic even though it is hyper-osmolal with respect to blood.

B. Pulmonary Formulations

In some embodiments, mucus penetrating nanoparticles (MPP) are formulated for pulmonary administration. Both dry powder and liquid formulations can be used to form aerosol formulations. The term aerosol as used herein refers to any preparation of a fine mist of particles, which can be in solution or a suspension, whether or not it is produced using a propellant. Dry powder formulations can be administered via pulmonary inhalation to a patient without the benefit of any carrier, other than air or a suitable propellant.

The pharmaceutical carrier may include a bulking agent or a lipid or surfactant. Natural surfactants such as dipalmitoylphosphatidylcholine (DPPC) are the most preferred. Synthetic and animal derived pulmonary surfactants include Exosurf—a mixture of DPPC with hexadecanol and tyloxapol added as spreading agents, Pumactant (Artificial Lung Expanding Compound or ALEC)—a mixture of DPPC and PG, KL-4—composed of DPPC, palmitoyl-oleoyl phosphatidylglycerol, and palmitic acid, combined with a 21 amino acid synthetic peptide that mimics the structural characteristics of SP-B, Venticute—DPPC, PG, palmitic acid and recombinant SP-C, Alveofact—extracted from cow lung lavage fluid, Curosurf—extracted from material derived from minced pig lung, Infasurf—extracted from calf lung lavage fluid, and Survanta—extracted from minced cow lung with additional DPPC, palmitic acid and tripalmitin. Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride. Dry powder formulations are typically prepared by blending one or more mucus penetrating nanoparticles with one or more pharmaceutically acceptable carriers. Optionally, additional active agents may be incorporated into the mixture as discussed below. The mixture is then formed into particles suitable for pulmonary administration using techniques known in the art, such as lyophilization, spray drying, agglomeration, spray coating, coacervation, low temperature casting, milling (e.g., air-attrition milling (jet milling), ball milling), high pressure homogenization, and/or supercritical fluid crystallization.

In certain embodiments, mucus penetrating nanoparticles (MPP) are formulated for administration as an aerosol. The dry powder and liquid formulations described above can be used to form aerosol formulations for pulmonary administration. Aerosols for the delivery of therapeutic and/or other active agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

In some cases, a device is used to administer the formulations to the lungs. Suitable devices include, but are not limited to, dry powder inhalers, pressurized metered dose inhalers, nebulizers, and electrohydrodynamic aerosol devices. Inhalation can occur through the nose and/or the mouth of the patient. Administration can occur by self-administration of the formulation while inhaling or by administration of the formulation via a respirator to a patient on a respirator.

C. Topical and Ophthalmic Formulations

In certain embodiments, mucus penetrating nanoparticles (MPP) are formulated for administration to the mucosal surface of the eye. Topical or enteral formulations can be prepared as aqueous compositions using techniques is known in the art. Typically, such compositions can be prepared as solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, emulsomes, sprays, gels, creams or ointments.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include agents, for example, sugars or sodium chloride, to adjust the tonicity.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combinations thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for administration upon reconstitution. Suitable buffers include, but are not limited to, phosphate buffers, acetate buffers, and citrate buffers.

Water soluble polymers are often used in pharmaceutical formulations. Suitable water-soluble polymers include, but are not limited to, polyvinylpyrrolidone, dextran, carboxymethylcellulose, and polyethylene glycol. Sterile solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for ocular administration are preferably in the form of a sterile aqueous solution or suspension of particles formed from one or more polymer-drug conjugates. Acceptable solvents include, for example, water, Ringer's solution, osmolar (PBS), and iso-osmolar sodium chloride solution, which are then adjusted to the desired hypotonicity for the eye as determined using MPP to observe osmotically-induced flow of water (tear fluid). The formulation may also be a sterile solution, suspension, or emulsion in a nontoxic, parenterally acceptable diluent or solvent such as 1,3-butanediol.

In some instances, the formulation is distributed or packaged in a liquid or semi-solid form such as a solution (eye drops), suspension, gel, cream or ointment. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Examples of useful buffers are acetate, borate, carbonate, citrate, and phosphate buffers. Solutions, suspensions, or emulsions for ocular administration may also contain one or more tonicity agents to adjust the tonicity of the formulation to be in the moderately hypotonic range. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known in the art, such as dispersing agents, wetting agents, and suspending agents.

In still other embodiments, the nanoparticles are formulated for topical administration to mucosa. Suitable dosage forms for topical administration include creams, ointments, salves, sprays, gels, lotions, and emulsions.

The formulation may contain one or more excipients, such as emollients, surfactants, and emulsifiers. "Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

In some embodiments, the mucus penetrating nanoparticles are formulated with one or more surfactants. Surfactants are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

In some embodiments, the mucus penetrating nanoparticles are formulated with one or more emulsifiers. Emulsifiers are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

In some embodiments, the mucus penetrating nanoparticles are formulated as an "oil". Oil is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

In some embodiments, the mucus penetrating nanoparticles are formulated with as an emulsion. An emulsion is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

In some embodiments, the mucus penetrating nanoparticles are formulated as a lotion. A lotion is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

In some embodiments, the mucus penetrating nanoparticles are formulated with as a cream. A cream is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

In some embodiments, the mucus penetrating nanoparticles are formulated as an ointment. An ointment is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

In some embodiments, the mucus penetrating nanoparticles are formulated as a gel. A gel is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

In some embodiments, the mucus penetrating nanoparticles are formulated as a foam. Foams consist of an emulsion in combination with a gaseous propellant or gas-emitting component. In some embodiments, the mucus penetrating nanoparticles are formulated with one or more buffers that are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7.

D. Enteral Formulations

In some embodiments, the mucus penetrating nanoparticles are formulated for enteral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations may be prepared using one or more pharmaceutically acceptable excipients, including diluents, preservatives, binders, lubricants, disintegrators, swelling agents, fillers, stabilizers, and combinations thereof.

Excipients, including plasticizers, pigments, colorants, stabilizing agents, and glidants, may also be used to form coated compositions for enteral administration. Delayed release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, P A: Williams and Wilkins, 1995). These references provide information on excipients, materials, equipment and process for preparing tablets and capsules and delayed release dosage forms of tablets, capsules, and granules.

The capsules may be coated, for example to delay release once the particles have passed through the acidic environment of the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

IV. Methods of Making

Techniques for making nanoparticles are known in the art and include, but are not limited to, solvent evaporation, solvent removal, spray drying, phase inversion, low temperature casting, and nanoprecipitation, for example, as described in WO/2013/110028.

In some embodiments the nanoparticles are formed by emulsion of one or more core polymers, one or more surface altering materials, and one or more low molecular weight emulsifiers. For example, in some embodiments the nanoparticles are made by dissolving one or more core polymers in an organic solvent, adding the solution of one or more core polymers to an aqueous solution or suspension of the emulsifier to form an emulsion, and then adding the emulsion to a second solution or suspension of the emulsifier to effect formation of the nanoparticles.

Pharmaceutically acceptable excipients, including pH modifying agents, disintegrants, preservatives, and antioxidants, can optionally be incorporated into the particles during particle formation. As described above, one or more additional active agents can also be incorporated into the nanoparticle during particle formation. One or more surface modifying agents are also incorporated into the particle either during particle formulation and/or attached subsequently to the surface of particles.

V. Methods of Use

It has been established that nanoparticles densely coated with high molecular weight poly(ethylene) glycol can penetrate mucus for the delivery of therapeutic, prophylactic, nutraceutical and/or diagnostic agents to a subject.

The MPPs are directly administered to a specific bodily location of the subject. For example, in some embodiments the MPPs are delivered directly to the mucosal surface of the eye, the vagina, the digestive tract, the colon, the rectum, the mouth, the nose, the ear or the lungs. In some embodiments, the MPPs are administered by topical administration directly onto or into the mucosa. In further embodiments, the route of administration targets the MPPs directly to a specific organ.

Pharmaceutical compositions including MPPs can be administered in a variety of manners, depending on whether local or systemic administration is desired, and depending on the area to be treated.

Compositions of MPPs can be administered during a period before, during, or after onset of symptoms of a disease, or any combination of periods before, during or after onset of one or more disease symptoms.

The term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease or disorder, and the treatment being effected.

The effect of MPPs can be compared to a control. Suitable controls are known in the art and include, for example, untreated cells or an untreated subject. In some embodiments, the control is untreated tissue from the subject that is treated, or from an untreated subject. Preferably the cells or tissue of the control are derived from the same tissue as the treated cells or tissue. In some embodiments, an untreated control subject suffers from, or is at risk from the same disease or condition as the treated subject. For example, in some embodiments, an untreated control subject does not receive the desired therapeutic, prophylactic or diagnostic effect imparted by the MPPs.

The present invention will be further understood by reference to the following non-limiting examples.

EXAMPLES

Example 1

Reaction Buffer Affects the Coating Density of High Molecular Weight PEG

Materials and Methods

Nanoparticle (NP) Coating Methods

PEG-coated nanoparticles were synthesized using the two methods previously described (Nance et al., Sci Transl Med, 2012, 4, 149-119). For the "MES buffer method", excess methoxy-polyethylene glycol (mPEG)-amine (10 kDa) was dissolved in 50 mM 2-(N-morpholino)ethanesulfonic acid (MES) buffer (Sigma) at pH 6. Carboxylate-modified polystyrene (PS) nanoparticles with a size of 200 nm (Molecular Probes) were added to the MES/PEG solution and sonicated for 10 min. 1-ethyl-3-(3-dimethylaminopropyl)-carbodiimide (EDC, Sigma) and N-Hydroxysulfosuccinimide (NHS, Sigma) were added at a ratio of 0.1:1:1:1 COOH:PEG:EDC:NHS. The mixture was incubated at 37° C. overnight, and then the nanoparticles were collected by centrifugation and washed twice with DI water. For the "borate buffer method", 40 nm, 100 nm, or 200 nm carboxylate-modified PS nanoparticles (Molecular Probes) were coated with polyethylene glycol (PEG) with molecular weight of 5 kDa, 10 kDa, 20 kDa, or 40 kDa. PS nanoparticles were suspended in 200 mM borate buffer (pH 7.4), and methoxy-PEG-amine was added in excess. Excess amounts of NHS and EDC were added. The nanoparticle mixtures were incubated at room temperature overnight and subsequently washed twice with DI water.

Characterization of Formulated Nanoparticles

Nanoparticles were suspended in a 10 mM NaCl solution, and characterized for size and -potential with dynamic light scattering (DLS) and laser Doppler anemometry, respectively, using a Zetasizer Nano ZS90 (Malvern Instruments). DLS was performed at 90° scattering angle, and all measurements were taken at 25° C., in accordance with the instrument settings.

Results

Figure 2A:
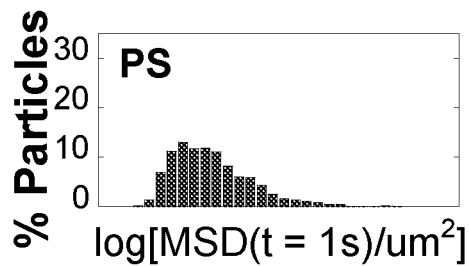
FIG. 2A shows the distributions of the logarithms of individual particle MSD of 200 nm PS at a time scale of 1 second.
Figure 2B:
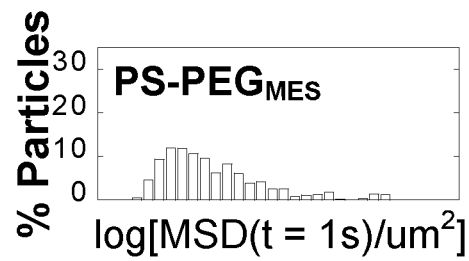
FIG. 2B shows the distributions of the logarithms of individual particle MSD of PS-PEG NP coated with 10 kDa PEG using the MES method at a time scale of 1 second.
Figure 2C:
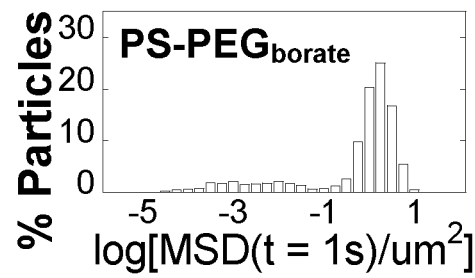
FIG. 2C shows the distributions of the logarithms of individual particle MSD of PS-PEG NP coated with 10 kDa PEG using the borate method at a time scale of 1 second.

In the grafting of 10 kD PEG onto the surface of PS nanoparticles (PS NP), reaction buffers of MES and borate buffer were compared. PS NP coated with 10 kDa PEG using the MES method (PS-PEG$_{MES}$, 220±10 nm; −12±0.4 mV) were adhesively immobilized in CVM; the ensemble averaged mean squared displacement (<MSD>) for PS-PEG$_{MES}$ NP was >10,000 fold slowed in mucus compared to the theoretical diffusion rates of similarly sized nanoparticles in water (Table 1). In contrast, the same PS NP coated with 10 kDa PEG using the borate method (PS-PEG$_{borate}$, 260±7 nm; −0.7±0.5 mV) rapidly diffused in CVM. The ensemble-averaged mean squared displacement, <MSD>, of PS-PEG$_{borate}$ NP was only 11-fold slowed in CVM compared to their theoretical diffusion rate in water, MSD$_w$ (Table 1, FIG. 1), and ~1,000-fold higher than either uncoated PS NP (180±1 nm; −59±2 mV) or PS-PEG$_{MES}$ (FIG. 1, Table 1). The <MSD> (FIG. 1) and the logarithmic distribution of individual MSD values (FIG. 2A, FIG. 2B) for PS-PEG$_{MES}$ NP were similar to uncoated PS nanoparticles, as we reported previously (Wang et al., Angew Chem Int Ed Engl, 2008, 47, 9726-9729). The logarithmic distribution of individual MSD values for PS-PEG$_{borate}$ NP were much greater than uncoated PS nanoparticles and PS-PEG$_{MES}$ NP (FIG. 2C). Nanoparticle trajectories representing 3 seconds of movement in CVM further emphasize the difference in transport behavior, as the motion of PS-PEG$_{borate}$ NP reflected diffusive motion, while the trajectories of PS and PS-PEG$_{MES}$ NP were highly constrained (FIGS. 3A-3C).

TABLE 1

Size, ζ-potential, PEG surface density (area covered by PEG/total surface area, or Γ/SA), and the comparison of the ensemble averaged MSD in mucus (<MSD>) to the theoretical MSD of similarly sized particles in water (MSD$_w$) of 100 and 200 nm PS and PS-PEG NP prepared by various methods.

| Size (nm) | Type | PEG MW (kDa) | Hydrodynamic diameter (nm) | ζ-potential (mV) | Γ/SA | # PEG chains/ 100 nm$^2$ | MSD$_w$/<MSD> |
|---|---|---|---|---|---|---|---|
| 40 | PS | — | 56 ± 2 | −33 ± 0.6 | NA | NA | NA |
|  | PS-PEG | 5 | 60 ± 1 | −2.2 ± 0.2 | NA | NA | NA |
|  |  | 10 | 68 ± 0.4 | −2.9 ± 0.4 | NA | NA | NA |
|  |  | 20 | 84 ± 3 | −2.6 ± 0.2 | NA | NA | NA |
|  |  | 40 | 97 ± 1 | −3.4 ± 0.5 | NA | NA | NA |
| 100 | PS | — | 90 ± 1 | −51 ± 1.6 | 0 | 0 | >10,000 |
|  | PS-PEG | 5 | 110 ± 2 | −3.1 ± 0.3 | >2* | ~9* | 10 |
|  |  | 10 | 120 ± 7 | −0.5 ± 0.1 | 2.0 ± 0.1 | 4.4 ± 0.2 | 18 |
|  |  | 20 | 130 ± 4 | −0.4 ± 0.1 | 3 ± 0.1 | 3.3 ± 0.1 | 6 |
|  |  | 40 | 170 ± 8 | −1 ± 0.1 | 2.1 ± 0.2 | 1.2 ± 0.1 | 20 |
| 200 | PS | — | 180 ± 1 | −59 ± 2 | 0 | 0 | >10,000 |
|  | PS-PEG | 5 | 230 ± 5 | −1.6 ± 0.1 | 1.6 ± 0.1 | 7.1 ± 0.4 | 9 |
|  |  | 10 | 260 ± 7 | −0.7 ± 0.5 | 1.5 ± 0.1 | 3.3 ± 0.1 | 11 |
|  |  | 10 (MES) | 220 ± 10 | −12 ± 0.4 | 1.3 ± 0.1 | 2.9 ± 0.3 | >10,000 |
|  |  | 20 | 270 ± 7 | −2 ± 0.7 | 1.7 ± 0.1 | 1.9 ± 0.2 | 10 |
|  |  | 40 | 300 ± 5 | −1 ± 0.6 | 1.7 ± 0.1 | 1 ± 0.1 | 15 |

*based on Nance et al., Sci Transl Med, 2012, 4, 149-119.

Unless otherwise indicated, PS-PEG NP were prepared via the borate method. Values are averaged over n ≥ 3 samples.

Example 2

Density of Coated 10 kD PEG on the Surface of PS NPs

Materials and Methods
Measurements of PEG Surface Density

PEG density was calculated as previously described (Nance et al., Sci Transl Med, 2012, 4, 149-119; Xu et al., J Control Release, 2013, 170, 279-286). Briefly, nanoparticles were fully dissolved in deuterated chloroform ($CDCl_3$, Sigma), trifluoroacetic acid-d (TFAd, Sigma), and a known concentration of Tetramethylsilane (TMS, 1% w/v). H-NMR spectra were obtained using a Bruker REM400 at 400 mHz. PEG density, or $\Gamma/SA$, was calculated from the integral of the PEG peak (3.6 ppm) and the internal standard TMS peak (0 ppm). To calculate the area occupied by the PEG chains on each particle, a random walk statistics model was used to find the area occupied by PEG of a certain length. These calculations yield a sphere with diameter $d=0.76 \ (m_b)^{0.5}$ where $m_b$ is the molecular weight of the PEG in question, yielding an area occupied by PEG of $A=\pi(d/2)^2$ (Boylan et al., J Control Release, 2012, 157, 72-79). The areas occupied were then used to calculate the number of PEG chains per 100 $nm^2$ and area occupied by PEG chains/total particle surface area ($\Gamma/SA$). PEG 5 kDa was used for calibrating PEG concentration in solution. For PEG surface density calculations, it was assumed that the nanoparticles' surfaces were smooth and their diameter is equivalent to that measured by DLS.

Results

In the quantification of the PEG surface density on the PS-PEG NP, a quantitative NMR method was used to infer the physical conformation of the PEG chains based on the packing density ($\Gamma/SA$, where $\Gamma$ is the unconstrained surface area that would be covered by the grafted PEG chains and SA is the total nanoparticle surface area) (Nance et al., Sci Transl Med, 2012, 4, 149-119; Xu et al., J Control Release, 2013, 170, 279-286). The $\Gamma/SA$ for the PS-$PEG_{borate}$ NP (1.5±0.0) was increased compared to 1.3±0.1 for PS-$PEG_{MES}$ NP (Table 1), indicating that the PEG chains were more densely packed on the surfaces of the PS-$PEG_{borate}$ NP. The $\Gamma/SA$ values correspond to 3.3±0.1 10 kDa PEG chains per 100 $nm^2$ for PS-$PEG_{borate}$ NP, compared to 2.9±0.3 10 kDa PEG chains per 100 $nm^2$ for PS-$PEG_{MES}$ NP. Previously, an indirect method to quantify PEG surface density was used involving the conjugation of fluorescent dyes to the unreacted carboxylic acid groups remaining on the nanoparticle surface after the PEG conjugation (Wang et al., Angew Chem Int Ed Engl, 2008, 47, 9726-9729). In this indirect method, approximately ~69% of carboxylic acid groups on the PS NP surface were conjugated to 2 kDa PEG, and ~65% of the carboxylic acid groups on the PS NP surface were conjugated to 10 kDa PEG (Wang et al., Angew Chem Int Ed Engl, 2008, 47, 9726-9729).

Results from the quantitative NMR method and calculation implies that there is a minimum PEG density threshold that must be exceeded to effectively shield the PS NP surface from interactions with CVM, and that there is a narrow margin between where the coating is sufficient or insufficient.

Similarly, results from Nance et al., Sci Transl Med, 2012, 4, 149-119 further implies that the required density of the PEG coating also depends on nanoparticle size and PEG MW. A $\Gamma/SA$ of at least 2.0 was required for 100 nm PS nanoparticles coated with 5 kDa PEG to effectively penetrate through the brain extracellular matrix (Nance et al., Sci Transl Med, 2012, 4, 149-119), whereas $\Gamma/SA=1.7$ was an insufficient coating.

The PEG coating density is achieved at different levels depending on the process and substrates of the reaction. Xu et al., J Control Release, 2013, 170, 279-286 observed that biodegradable nanoparticles composed of block copolymers of PEG (MW as high as 10 kDa) and poly(lactic-co-glycolic acid) (PLGA-PEG) were sufficiently densely coated with PEG to allow rapid diffusion in human CVM. Since the PLGA-PEG nanoparticles were formed using an emulsion method that allowed PEG to partition to the nanoparticle surface during the slow hardening process, rather than grafting PEG onto the surface of preformed nanoparticles, $\Gamma/SA$ values of 2.3 and greater ($\Gamma/SA=3.0$ for 10 kDa PEG) were achieved (Xu et al., J Control Release, 2013, 170, 279-286).

Example 3

High Molecular Weight (HMW) PEG in a Dense Coating Facilitates Mucus Penetration of Particles Materials and Methods
Nanoparticle (NP) Coating Formulation Nanoparticles were prepared as described by Nance et al., Sci Transl Med, 2012, 4, 149-119; Lai et al., Proc Natl Acad Sci USA, 2007, 104, 1482-1487. Briefly, 40, 100 and 200 nm carboxylate-modified polystyrene (PS) beads were coated with 5 kDa up to 40 kDa methoxy-PEG-amine using the specified buffer.

Multiple particle tracking in human cervicovaginal mucus

Human cervicovaginal mucus (CVM) samples were obtained as previously described (Lai et al., Proc Natl Acad Sci USA, 2007, 104, 1482-1487; Boskey et al., Sex Transm Dis, 2003, 30, 107-109). Briefly, undiluted CVM from women with normal vaginal microbiota was obtained using a self-collection method with a menstrual fluid collection device following a protocol approved by the Institutional Review Board of the Johns Hopkins Medical Institution. Mucus samples were stored at 4° C. prior to use, and used within 4 h of collection. Up to 24 of particle solution (0.02-0.08% w/v) was added to a volume of 304 CVM in a custom made well. Wells were sealed with a coverslip that was affixed with superglue. Movies were obtained with a 100×/1.46 NA oil-immersion objective via an EMCCD camera (Evolve 512; Photometrics) as part of an inverted epifluorescence microscope setup (Zeiss Axio Observer). Movies were captured with Metamorph software (Molecular Devices) at a temporal resolution of 66.7 ms for 20 s. Nanoparticle trajectories and mean squared displacements (MSD) were obtained using MATLAB (Schuster et al., Biomaterials 2013, 34, 3439-3446) with a minimum of 30 frames tracked for each particle, and MSD calculated as $<\Delta r^2(\tau)>=[x(t+\tau)-x(t)]^2+[y(t+\tau)-y(t)]^2$ ($\tau$=time scale or time lag) (Lai et al., Proc Natl Acad Sci USA, 2007, 104, 1482-1487; Suh et al., Adv Drug Deliv Rev, 2005, 57, 63-78; Dawson et al., Biotechnol Prog, 2004, 20, 851-857). At least 150 particles were tracked in n=3 independent samples. Our prior work has indicated that static error can be estimated to be below 20 nm, much smaller than the average particle displacement (Suh et al., Adv Drug Deliv Rev, 2005, 57, 63-78; Suk et al., J Control Release, 2014, 178, 8-17).

Results 200 nm PS NP coated with 5-40 kDa PEG using the borate method (PS-$PEG_{5-40 \ kDa}$, final sizes 230-300 nm, Table 1) were able to rapidly penetrate CVM, as indicated by the high <MSD> values measured (FIG. 4). In addition, the 3-second trajectories for all PS-PEG$_{5-40\ kDa}$ NP reflected diffusive behavior, in stark contrast to the uncoated PS NP (FIGS. 5A-5E). The PS-PEG$_{5-40\ kDa}$ NP also had high PEG density, Γ/SA≥1.5 (Table 1). It was evident that the number of PEG molecules per 100 nm² decreased as the PEG MW increased, which can be attributed to the increased amount of space occupied by each PEG chain as the MW increases; the area occupied by one unconstrained 5 kDa PEG chain is ~23 nm², compared to ~180 nm² for unconstrained 40 kDa PEG molecules. Additionally, the hydrodynamic diameter of the nanoparticles after PEGylation increased as the PEG MW increased; dense packing of the PEG chains causes elongation, so higher MW PEG chains would create a thicker corona.

It is hypothesized that by densely packing the PEG chains on the nanoparticle surface, the PEG becomes aligned and sterically restricted from penetrating into the mucin gel, regardless of PEG MW. Adhesion has been shown to depend on PEG chain movement, and thus if chains are constrained enough, they will not be able to interpenetrate with the mucus mesh, leading to decreased mucoadhesion (Huang et al., J Control Release, 2000, 65, 63-71).

Yang and coworkers found that <20% of nanoparticles coated with up to 20 kDa PEG were cleared from systemic circulation for Γ/SA>2.8. At this PEG surface density, they determined that neighboring PEG chains were highly unlikely to simultaneously reach an extended configuration, which could expose the particle surface to protein adsorption. In addition, they found that even a minor decrease in PEG density led to a decrease in systemic circulation time to <2 h (Yang et al., Mol Pharm, 2014, 11, 1250-1258). Similarly, we found that a small decrease in nanoparticle PEG surface density resulted in a transition from non-mucoadhesive surface properties to mucoadhesive surface properties.

Example 4

The Core Size of Nanoparticles Affects PEG Coating Density and Mucus Penetration Materials and Methods Nanoparticles were prepared as described by Nance et al., Sci Transl Med, 2012, 4, 149-119; Lai et al., Proc Natl Acad Sci USA, 2007, 104, 1482-1487. Briefly, 40, 100 and 200 nm carboxylate-modified polystyrene (PS) beads were coated with 5 kDa up to 40 kDa methoxy-PEG-amine using the specified buffer.

Figure 6:
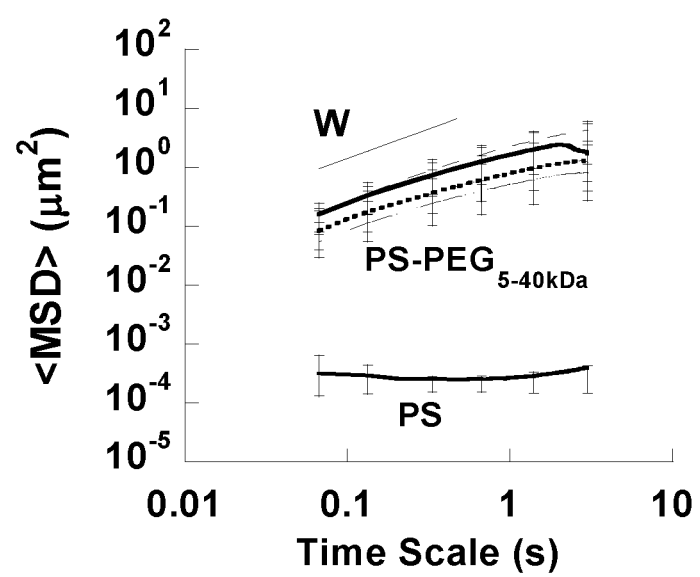
FIG. 6 shows the ensemble averaged mean-squared displacement (<MSD>) in human cervicovaginal mucus as a function of time for 100 nm PS and PS-PEG NP coated with 5 kDa, 10 kDa, 20 kDa, or 40 kDa PEG using the borate method, including the theoretical MSD of 100 nm particles (size of PS-PEG$_{10\ kDa}$) in water (W).

Results 100 nm PS NPs were coated with 5 kDa-40 kDa PEG using the borate method (PS-PEG$_{5-40\ kDa}$, final sizes 110-170 nm). Table 1 and FIG. 6 shows that Γ/SA values were all >2 for 100 nm PS-PEG$_{5-40\ kDa}$ NP, resulting in rapid NP diffusion through CVM. PEG-coated nanoparticle trajectories reflected diffusive motion, in stark contrast to the uncoated PS (FIGS. 7A-7E). All 100 nm and 200 nm PS-PEG$_{5-40\ kDa}$ NP formulations were slowed <20 fold in CVM compared to their theoretical diffusion rates in water (Table 1).

It is hypothesized that by densely packing the PEG chains on the nanoparticle surface, the PEG becomes aligned and sterically restricted from penetrating into the mucin gel, regardless of PEG MW. Adhesion has been shown to depend on PEG chain movement, and thus if chains are constrained enough, they will not be able to interpenetrate with the mucus mesh, leading to decreased mucoadhesion (Huang et al., J Control Release, 2000, 65, 63-71).

Example 5

The Impact of PEG MW on the Distribution of Coated Particles In Vivo

Materials and Methods

Female CF-1 mice 6-8 weeks old were housed in a reverse light cycle facility (12 h light, 12 h dark) for one week to allow acclimatization. For vaginal distribution, mice were selected for naturally cycling estrus by visual appearance of their introitus as previously described (Champlin et al., Biol Reprod, 1973, 8, 491-494). The vagina of mice in the estrus phase is the most similar to the human vagina (Asscher et al., J Anat, 1956, 90, 547-552; Smith et al., Am J Anat, 1934, 54, 27-85), and their cervicovaginal mucus has similar barrier properties to human CVM (Ensign et al., Mol Pharm, 2013, 10, 2176-2182). For colorectal distribution, mice were starved for 24 h, as this leads to less frequent, softer pellets (Maisel et al., J Control Release, 2015, 10, 197, 48-57, Epub 2014 Nov. 4). Mice were anesthetized using isoflurane, and 5 μL (intravaginal) or 20 μL (intrarectal) of 0.02% w/v of 100 nm (intravaginal) or 40 nm (intrarectal) nanoparticles in DI water were administered (Maisel et al., J Control Release, 2015, 10, 197, 48-57, Epub 2014 Nov. 4; Ensign et al., Sci Transl Med, 2012, 4, 138-179; Maisel et al., J Control Release, 2015, 209, 280-287). Mice were sacrificed after 5-10 min, and the tissues were excised and flash-frozen in Tissue-Tek O.C.T. Compound. Tissues were sectioned into 6 μm slices along the entire length of the vagina and colorectum with a Leica CM-3050-S cryostat. Slices were fixed with 10% formalin and stained using ProLong Gold anti-fade® reagent with DAPI to stain nuclei and retain particle fluorescence. Images were obtained using the inverted epifluorescence microscope setup (Zeiss Axio Observer). All experiments were approved by the Johns Hopkins University Animal Care and Use Committee.

Results

PS-PEG NPs densely coated with various MW PEG (5 kDa, 10 kDa, 20 kDa, 40 kDa) were distributed uniformly in the cervicovaginal tract and colorectum of mice, observed in transverse vaginal and colorectal tissue cryosections obtained 5-10 min after administration of solutions containing coated PS-PEG NPs. PS-PEG NPs were administered of the appropriate sizes that Applicant's previously observed distribute uniformly in the mouse vagina (~100 nm) and colorectum (~40 nm) when they are sufficiently well PEGylated and administered in a hypotonic vehicle that induces fluid absorption by the epithelium (Ensign et al., Sci Transl Med, 2012, 4, 138-179; Ensign et al., Biomaterials, 2013, 34, 6922-6929; Maisel et al., J Control Release, 2015, 10, 197, 48-57, Epub 2014 Nov. 4; Maisel et al., J Control Release, 2015, 209, 280-287). Similar to Applicant's prior observations, uncoated PS NP aggregated in the luminal mucus layers, but all PS-PEGNP formulations with sufficiently dense PEG coatings for diffusion in ex vivo mucus samples (PS-PEG$_{5-40\ kDa}$) were transported rapidly and uniformly to the vaginal and colorectal epithelial surfaces in vivo. This result is consistent with previous observations that the diffusion of nanoparticles in mucus ex vivo correlates well with the observed distribution at mucosal surfaces in vivo, i.e., particles that diffuse rapidly/unhindered in mucus ex vivo also distribute much more uniformly over mucosal surfaces and then persist longer when they are administered locally to a mucosal tissue. Improved nanoparticle distribution provides more efficacious treatment and prevention of diseases at mucosal sites, including prevention of herpes (HSV-2) infection in the cervicovaginal tract, prevention of asthma-induced lung inflammation, and treatment of cervical cancer (Ensign et al., Sci Transl Med, 2012, 4, 138-179; Suk et al., J Control Release, 2014, 178, 8-17; Yang et al., Adv Healthc Mater, 2014, 3, 1044-1052; da Silva et al., J Control Release, 2014, 180, 125-133)

We claim:

1. Mucus penetrating particles for the delivery of a therapeutic, prophylactic, or diagnostic agent through the mucosa to the underlying epithelium of a subject, comprising:
   one or more core polymers forming the particles;
   one or more therapeutic, prophylactic and/or diagnostic agents; and
   one or more surface modifying polymers comprising a polyethylene oxide polymer, wherein the polyethylene oxide polymer has a molecular weight from greater than 10 kDa to about 40 kDa,
   wherein the surface modifying polymers are covalently bound to the core polymers prior to formation of the particles so that they are aligned and sterically restricted on the surface of the particles and are in a sufficient density, when measured by $^1$H NMR, of from about 0.9 to about 100 molecules/100 nm$^2$,
   effective to enhance the mucosal diffusion of the modified particles relative to particles that are not surface modified by binding of surface modifying polymers to the core polymers,
   wherein the particles have a hydrodynamic diameter of between about 50 nm and 500 nm, inclusive, and
   wherein the particles are not in a hypotonic formulation for application to the mucosa on epithelial tissue other than water.

2. The mucus penetrating particles of claim 1, wherein the surface modifying polymer is a poly(ethylene glycol) or a copolymer thereof.

3. The mucus penetrating particles of claim 2, wherein the surface density of poly(ethylene glycol), when measured by 1H NMR is between about 0.9 and about 45 molecules/100 nm$^2$.

4. The mucus penetrating particles of claim 3, wherein the surface packing density of poly(ethylene glycol), is 1.5 or greater than 1.5 when measured as a function of the following formula:

Γ/SA=Surface packing density wherein Γ is the total surface area that can be covered by unconstrained poly(ethylene glycol), and SA is the total nanoparticle surface area.

5. The mucus penetrating particles of claim 1, wherein the one or more surface altering polymers are present in an amount effective to make the surface charge of the particles neutral or essentially neutral in physiological fluids.

6. The mucus penetrating particles of claim 1, wherein the particles have a zeta-potential of between about −10 mV and 10 mV, inclusive, between about −5 mV and 5 mV, inclusive, or between about −2 mV and 2 mV, inclusive.

7. The mucus penetrating particles of claim 1, wherein the core polymer is selected from the group consisting of poly(caprolactone), polyhydroxy acids, polyamino acids, polyanhydrides, and polyorthoesters.

8. The mucus penetrating particles of claim 7, wherein the core polymer is a polyhydroxy acid selected from the group consisting of poly(lactic acid), poly(L-lactic acid), poly(glycolic acid), poly(lactic acid-co-glycolic acid), poly(L-lactic acid-co-glycolic acid), poly(D,L-lactide), poly(D,L-lactide-co-caprolactone), poly(D,L-lactide-co-caprolactone-co-glycolide), poly(D,L-lactide-co-PEO-co-D,L-lactide), and poly(D,L-lactide-co-PPO-co-D,L-lactide).

9. The mucus penetrating particles of claim 7, wherein the core polymer is covalently bound to the surface modifying polymer via an amine group on the surface modifying polymer.

10. The mucus penetrating particles of claim 1, wherein the particles have a hydrodynamic diameter of between about 60 nm and 300 nm, inclusive.

11. The mucus penetrating particles of claim 1, further formulated with a pharmaceutically acceptable excipient for administration into or onto the body via a route selected from the group consisting of enteral, parenteral, and topical administration.

12. The mucus penetrating particles of claim 1, wherein the polyethylene oxide polymer is covalently bound to the terminus of the block copolymer.

13. A method of administering one or more therapeutic, prophylactic, and/or diagnostic agents to a subject in need thereof, the method comprising administering to the subject an effective amount of the particles of claim 1.

14. The method of claim 13, wherein the particles are administered via a route selected from the group consisting of enterally, parenterally, and topically.

15. The method of claim 14, wherein the particles are administered to mucosal epithelium at a location selected from the group consisting of the vaginal epithelium, colorectal tract, ophthalmic epithelium, respiratory tract, mouth and combinations thereof.

16. The method of claim 15, wherein the particles are administered to cervicovaginal mucus, colorectal mucous, or mucus in the upper or lower respiratory tract.

* * * * *